United States Patent
Yamamoto et al.

[11] Patent Number: 6,107,504
[45] Date of Patent: Aug. 22, 2000

[54] ESTER GROUP-CONTAINING SILOXANE COMPOUND, AND ITS PREPARATION METHOD

[75] Inventors: Yuuichi Yamamoto; Koichi Ayama, both of Kumamoto, Japan

[73] Assignee: Chisso Corporation, Osaka, Japan

[21] Appl. No.: 09/181,608

[22] Filed: Oct. 28, 1998

[30] Foreign Application Priority Data

Dec. 26, 1997 [JP] Japan .................................. 9-368629

[51] Int. Cl.$^7$ ...................................................... C07F 7/08
[52] U.S. Cl. ............................................ 556/439; 549/215
[58] Field of Search ............................. 856/439; 549/215

[56] References Cited

U.S. PATENT DOCUMENTS

| | | | |
|---|---|---|---|
| 3,464,955 | 9/1969 | Bluestein | 556/439 |
| 3,965,150 | 6/1976 | Moeller | 556/439 |
| 5,326,844 | 7/1994 | Fujiki et al. | 556/439 |
| 5,475,126 | 12/1995 | Yoshida et al. | 556/439 |

OTHER PUBLICATIONS

Yoshihisa Kiso, et al., "Silicon Hydrides and Nickel Complexes", Journal of Organometallic Chemistry, vol. 50, (1973), pp. 297–310.

Iwao Ojima, et al., "Hydrosilylation of α,β–Unsaturated Nitriles and Esters Catalyzed by Tris(Triphenylphosphine)Chlororhodium",Journal of Organometallic Chemistry, vol. 111 (1976), pp. 43–60.

"Hydrosilation of α,β–Unsaturated Esters[1)]", Chem. Pharm. Bull., No. 11, (1974), pp. 2767–2769.

*Primary Examiner*—Paul F. Shaver
*Attorney, Agent, or Firm*—Oblon, Spivak, McClelland, Maier & Neustadt, P.C.

[57] ABSTRACT

There are herein disclosed a siloxane compound represented by the formula (1)

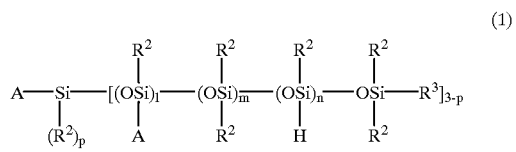

wherein $R^2$ is a methyl group or a phenyl group; $R^3$ is an alkyl group having 1 to 6 carbon atoms or A; l is an integer of 0 to 500; m is an integer of 0 to 1,000; n is an integer of 0 to 500; p is an integer of 0 to 2; and A is an ester group represented by the formula (2)

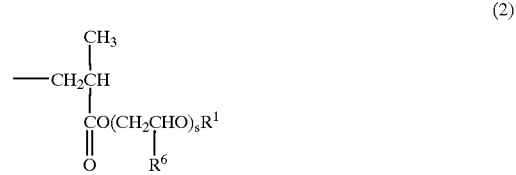

wherein $R^6$ is hydrogen or the methyl group; s is an integer of 0 to 100; and $R^1$ is a branched or a straight-chain alkyl group having 1 to 30 carbon atoms, a cyclohexyl group, a phenyl group, a benzyl group, a glycidyl group, or a fluorine-containing organic group represented by the formula (3)

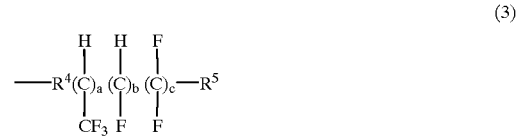

wherein $R^4$ is a saturated hydrocarbon having 0 to 6 carbon atoms, and when 0 is selected, $R^4$ is not present; $R^5$ is hydrogen or fluorine; a is 0 or 1; and b and c are each an integer of 0 to 20, but for a, b and c, 0 is not simultaneously selected, and a preparation method of the above siloxane compound.

14 Claims, No Drawings

ESTER GROUP-CONTAINING SILOXANE COMPOUND, AND ITS PREPARATION METHOD

BACKGROUND OF THE INVENTION

1. Field of the Invention

The present invention relates to an ester group-containing siloxane compound which can be blended with a coating composition, a binder, cosmetics or the like in order to improve its water repellency, lubricating properties and the like, and it also relates to a preparation method of the siloxane compound.

2. Description of the Related Art

Some methods for synthesizing ester group-containing silanes by a hydrosilylation of an acrylic acid ester or a methacrylic acid ester and a silane have heretofore been reported. For example, (a) Y. KISO; J. Organometal. Chem., Vol. 50, p. 297–310 (1973), (b) I. OJIMA; J. Organometal. Chem., Vol. 111, p. 43–60 (1976), and (c) E. YOSHII; Chem. Pharm. Bull., Vol. 22 (11), p. 2767–2769 (1974).

However, there has been no example in which the above hydrosilylation is carried out by the use of a siloxane compound in place of a silane under usual reaction conditions. In the case that the hydrosilylation is done by the use of the silane compound, several problems have been present. For example, a very specific catalyst needs to be used, and it is impossible to selectively produce a β-silyl compound. Accordingly, an ester group-containing siloxane compound cannot be prepared by the hydrosilylation using the silane compound under the usual conditions.

Furthermore, Japanese Patent Application Laid-open No. 291980/1995 discloses a method for preparing an ester group-containing silane by the hydrosilylation of methyl acrylate and the silane. However, any technique of using the siloxane compound has not been disclosed. According to this disclosed technique, an α-silyl compound in which a silicon-carbon bond can easily react with an alcohol can be selectively produced, but a chemically stably β-silyl compound cannot be selectively produced.

Because of the above situations, in a conventional case where the ester group-containing siloxane is prepared, a polysiloxane having a hydroxyl group or a carboxyl group at the terminal is used as a starting material, and an acid or an alcohol is reacted with this polysiloxane to obtain the ester.

However, the conventional preparation method proceeds via a terminal hydroxyl group-containing polysiloxane or a terminal carboxyl group-containing polysiloxane as described hereinbefore, and hence a preparation process is prolonged, which inconveniently leads to the increase of cost. Additionally, in the above esterification reaction, an acid catalyst is usually used, and owing to this acid catalyst, there is a problem that an undesirable side reaction such as the cleavage of a siloxane bond occurs.

SUMMARY OF THE INVENTION

In view of the above problems, the present inventors have intensively investigated with the intention of developing a method for preparing an ester group-containing siloxane compound which is a β-silyl compound. As a result, it has been found that when a methacrylic acid ester compound is reacted with a hydrosilyl group-containing siloxane compound, an ester group-containing siloxane compound having a novel structure can be prepared simply and inexpensively. The present invention has been completed on the basis of this knowledge.

Therefore, an object of the present invention is to provide a novel ester group-containing siloxane compound having a chemically stable β-silyl structure, and a simple and inexpensive method for preparing this siloxane compound.

The first aspect of the present invention is directed to a siloxane compound represented by the formula (1)

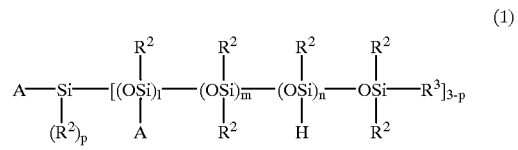

wherein $R^2$ is a methyl group or a phenyl group; $R^3$ is an alkyl group having 1 to 6 carbon atoms or A; l is an integer of 0 to 500; m is an integer of 0 to 1,000; n is an integer of 0 to 500; p is an integer of 0 to 2; and A is an ester group represented by the formula (2)

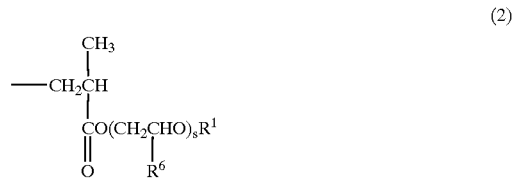

wherein $R^6$ is hydrogen or the methyl group; s is an integer of 0 to 100; and $R^1$ is a branched or a straight-chain alkyl group having 1 to 30 carbon atoms, a cyclohexyl group, a phenyl group, a benzyl group, a glycidyl group, or a fluorine-containing organic group represented by the formula (3)

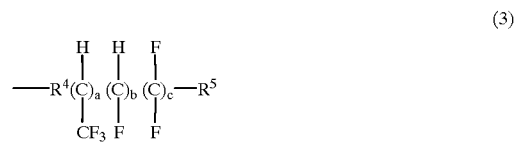

wherein $R^4$ is a saturated hydrocarbon having 0 to 6 carbon atoms, and when 0 is selected, $R^4$ is not present; $R^5$ is hydrogen or fluorine; a is 0 or 1; and b and c are each an integer of 0 to 20, but for a, b and c, 0 is not simultaneously selected.

The second aspect of the present invention is directed to a method for preparing an ester group-containing siloxane compound represented by the formula (1)

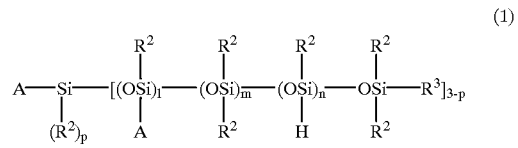

wherein $R^2$ is a methyl group or a phenyl group; $R^3$ is an alkyl group having 1 to 6 carbon atoms or A; l is an integer of 0 to 500; m is an integer of 0 to 1,000; n is an integer of 0 to 500; p is an integer of 0 to 2; and A is an ester group represented by the formula (2)

(2)

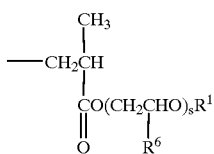

wherein $R^6$ is hydrogen or the methyl group; s is an integer of 0 to 100; $R^1$ is a branched or a straight-chain alkyl group having 1 to 30 carbon atoms, a cyclohexyl group, a phenyl group, a benzyl group, a glycidyl group, or a fluorine-containing organic group represented by the formula (3)

(3)

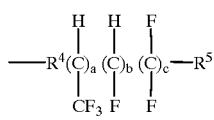

wherein $R^4$ is a saturated hydrocarbon having 0 to 6 carbon atoms, and when 0 is selected, $R^4$ is not present; $R^5$ is hydrogen or fluorine; a is 0 or 1; and b and c are each an integer of 0 to 20, but for a, b and c, 0 is not simultaneously selected, which comprises the step of reacting, in the presence of a platinum-containing catalyst, a methacrylic acid ester compound represented by the formula (4)

(4)

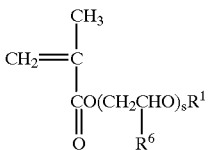

wherein $R^6$ is hydrogen or the methyl group; s is an integer of 0 to 100; and $R^1$ is a branched or a straight-chain alkyl group having 1 to 30 carbon atoms, a cyclohexyl group, a phenyl group, a benzyl group, a glycidyl group, or a fluorine-containing organic group represented by the formula (3)

(3)

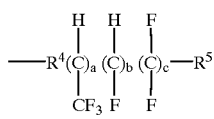

wherein $R^4$ is a saturated hydrocarbon having 0 to 6 carbon atoms, and when 0 is selected, $R^4$ is not present; $R^5$ is hydrogen or fluorine; a is 0 or 1; and b and c are each an integer of 0 to 20, but for a, b and c, 0 is not simultaneously selected, with a hydrosilyl group-containing siloxane compound represented by the formula (5)

(5)

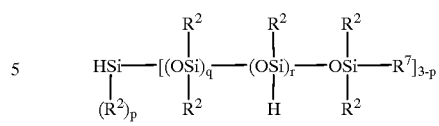

wherein $R^2$ is the methyl group or a phenyl group; $R^7$ is hydrogen or an alkyl group having 1 to 6 carbon atoms; q is an integer of 0 to 1000; r is an integer of 0 to 500; and p is an integer of 0 to 2.

According to the present invention, a chemically stable β-silyl compound can be selectively produced by reacting a methacrylic acid ester compound with a hydrosilyl group-containing siloxane compound in the presence of a platinum-containing catalyst. This β-silyl compound is an ester group-containing siloxane compound having a novel structure, and it can be prepared in a high purity and at a low cost by the method of the present invention.

DETAILED DESCRIPTION OF THE PREFERRED EMBODIMENTS

A methacrylic acid ester compound which can be used in the present invention can be represented by the formula (4). In this formula (4), s is an integer of 0 to 100, particularly preferably an integer of 1 to 30, because the compound in which s is an integer of 1 to 30 is easily available and products obtained from this kind of starting material can easily be utilized.

In the formula (4), $R^6$ is hydrogen or a methyl group.

$R^1$ is a branched or a straight-chain alkyl group having 1 to 30 carbon atoms, a cyclohexyl group, a phenyl group, a benzyl group, a glycidyl group, or a fluorine-containing organic group represented by the above formula (3). The number of the carbon atoms in the alkyl group is preferably in the range of 1 to 20, more preferably 1 to 10. The methacrylic acid ester compound in which the number of the carbon atoms in the alkyl group is more than 30 is not preferable, because such an ester compound is scarcely available and has a low reactivity.

A fluorine-containing organic group (3) can impart preferable characteristics such as water repellency and oil repellency to the siloxane compound of the present invention, and hence this group is a preferable organic group.

Typical examples of the methacrylic acid ester compound include methyl methacrylate, ethyl methacrylate, n-butyl methacrylate, iso-butyl methacrylate, tert-butyl methacrylate, isodecyl methacrylate, lauryl methacrylate, stearyl methacrylate, cyclohexyl methacrylate, ethylhexyl methacrylate, benzyl methacrylate, glycidyl methacrylate, butoxyethyl methacrylate, 2-{(1-propenyl)oxy}ethyl methacrylate, methoxypolyethylene glycol methacrylate, 2-phenoxyethyl methacrylate, 2,2,2-trifluoroethyl methacrylate, 2,2,3,3-tetrafluoropropyl methacrylate, 2,2,3,4,4,4-hexafluorobutyl methacrylate and β-(perfluorooctyl) ethyl methacrylate.

Above all, methyl methacrylate, ethyl methacrylate and n-butyl methacrylate are particularly preferable, because of having a high reactivity.

A hydrosilyl group-containing siloxane compound which can be used in the present invention can be represented by the formula (5). In this formula (5), $R^2$ is a methyl group or a phenyl group. The hydrosilyl group-containing siloxane compound in which $R^2$ is the methyl group of these functional groups has a low manufacturing cost and is easily available, and for these reasons, this kind of siloxane compound is preferable. $R^7$ is hydrogen or an alkyl group having 1 to 6 carbon atoms, particularly preferably 1 to 4 carbon atoms. The alkyl group in which the number of the carbon atoms is more than 6 is not preferable, because it is not easily available.

A symbol p is an integer of 0 to 2. In the case of p=2, the hydrosilyl group-containing siloxane compound can be obtained in a relatively high purity and is easily available. Therefore, the siloxane compound of p=2 is preferable.

A symbol q is an integer of 0 to 1000, preferably 0 to 500, more preferably 0 to 300. A symbol r is an integer of 0 to 500, preferably 0 to 300, more preferably 0 to 200. In the case that the values of p and q are outside the above range, such a hydrosilyl group-containing siloxane compound has a high viscosity and its handling is inconveniently difficult.

Typical examples of the hydrosilyl group-containing siloxane compound represented by the formula (5) include the following compounds. Incidentally, in the following formula, t is an integer of 1 to 1000, and u and v are each an integer of 0 to 500.

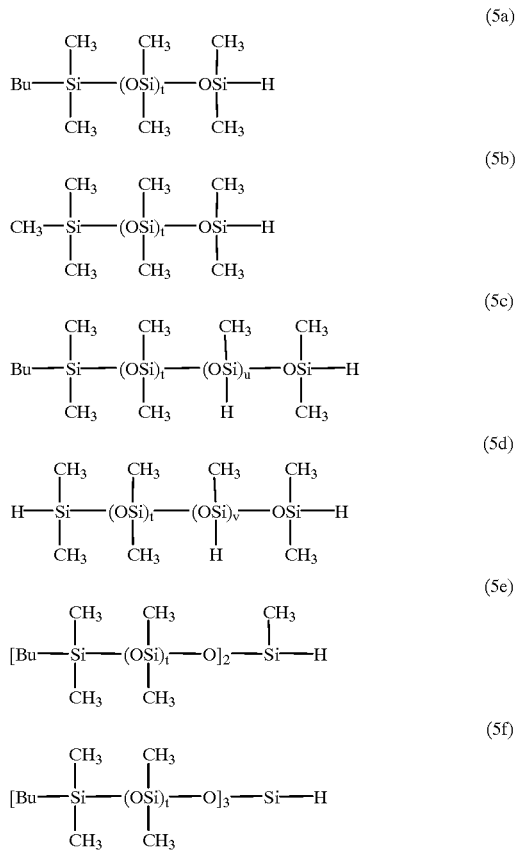

These siloxane compounds can each be synthesized by a usual procedure. Alternatively, the commercial products of these siloxane compounds can also be utilized.

A platinum-containing catalyst which can be used in the present invention is a platinum-based compound containing platinum. Examples of the platinum-containing catalyst include inorganic compounds including a platinum atom, platinum complexes, and catalysts obtained by supporting platinum on carriers. Typical examples of these catalysts include chloroplatinic acid, an isopropyl alcohol solution of chloroplatinic acid, bis(ethylene)platinum chloride, platinum (I) acetylacetonates and platinum-vinylsiloxane complexes. Above all, divinyltetramethyldisiloxane platinum complex, cyclovinylmethylsiloxane platinum complex and a vinylsiloxane complex of platinum mentioned in U.S. Pat. No. 3,715,334 can be preferably used.

No particular restriction is put on the amount of the platinum-containing catalyst, but it is preferably in the range of 0.1 to 10000 $\mu$mol, more preferably 1 to 1000 $\mu$mol in terms of platinum metal with respect to 1 mol of the hydrosilyl group-containing siloxane compound for the sake of economy and the proper progress of the reaction.

In the present invention, the siloxane compound represented by the formula (1) can be obtained by a hydrosilylation of the methacrylic acid ester represented by the formula (4) and the hydrosilyl group-containing siloxane compound represented by the formula (5) in the presence of the platinum-containing catalyst. The hydrosilylation occurs on all Si-H groups shown in the formula (5), though the degrees of the reaction are different at the respective Si-H groups. Therefore, between q and r in the formula (5) showing the starting material and l, m and n in the formula (1) showing the product, the relations of q=m and r=l+n are theoretically established, if other side reactions are not present.

A hydrosilylation temperature is preferably in the range of 10 to 120° C. However, when the boiling point of a selected starting material is relatively low, the starting material volatilizes on occasion. Moreover, when the reaction temperature is too low, much time is taken to complete the reaction. Accordingly, the reaction temperature is more preferably in the range of 50 to 80° C.

In the hydrosilylation, the employment of a polymerization inhibitor is optional. However, when the reaction temperature is 50° C. or more, it is preferable to use the polymerization inhibitor. Examples of the suitably usable polymerization inhibitor include 6-di-tert-butyl-4-methylphenol, 2,6-di-tert-butyl-4-ethylphenol, 2,6-di-tert-butylphenol, 2,2'-methylene-bis(6-tert-butyl-4-methylphenol), 1,3,5-trimethyl-2,4,6-tris(3,5-di-tert-butyl-4-hydroxybenzyl)benzene and monomethoxyhydroquinone. No particular restriction is put on the amount of the polymerization inhibitor, but it is preferably in the range of 0.0001 to 0.01 mol with respect to 1 mol of the methacrylic acid ester.

In the hydrosilylation, the employment of a solvent is optional. When the solvent is used, any solvent can be used, so long as it does not impair the catalytic function of the platinum-containing catalyst and does not have any reactivity to an Si-H bond. Examples of the suitably usable solvent include aromatic hydrocarbons such as toluene and xylene, saturated aliphatic hydrocarbons such as pentane, hexane and heptane, and ethers such as tetrahydrofuran and diethyl ether.

After completion of the reaction, a desired compound can be isolated from the obtained reaction mixture in a usual manner, followed by purification, to obtain the ester group-containing siloxane compound (1) of the present invention.

In the above formula (1), the configuration of the respective siloxane units in the polysiloxane skeleton includes both of a random configuration and a block configuration. Similarly, in the above formula (3), the configuration of fluoromethylene units also includes both of a random configuration and a block configuration.

Among the siloxane compound (1) of the present invention, the following compounds are particularly preferable from the viewpoints of the easy availability of the starting materials for the manufacture, an industrial utility and the like:

a. a siloxane compound of the present invention in which p=2 and n=0, b. a siloxane compound of the present invention in which p=2, l=0, n=0 and $R^2$=a methyl group, c. a siloxane compound of the present invention in which p=2, l=0, n=0, $R^2$=a methyl group, $R^3$=a butyl group and s=0, d. a siloxane compound of the present invention in which p=2, l=0, m=0, n=0, $R^2$=a methyl group and $R^3$=a methyl group, e. a siloxane compound of the present invention in which p=2, l=0, m=0, n=0, s=0, $R^2$=a methyl group and $R^3$=a methyl group, and f. a siloxane compound of the present invention in which p=2, l=0, n=0, $R^2$=a methyl group, $R^3$=A and s=0.

Next, the present invention will be described in more detail in accordance with examples, but the scope of the present invention should not be limited to these examples.

EXAMPLE 1

(Reaction of pentamethyldisiloxane and methyl methacrylate)

3.2 g (which corresponded to 1 wt % of a total feed) of 2,6-di-tert-butyl-4-methylphenol was placed in a 500 ml three-necked flask equipped with a stirring device and a condenser, and this flask was then purged with nitrogen. Furthermore, 200 ml of toluene, 63.8 g (0.64 mol) of methyl methacrylate and 86.08 g (0.58 mol) of pentamethyldisiloxane were added to the flask. While the temperature in the flask was maintained at 80° C., 218 μl (2.9×10$^{-5}$ mol, 5×10$^{-5}$ mol to Si—H) of [divinyltetramethyldisiloxane] platinum (0) complex (3 wt % xylene solution) represented by the following formula (I) was added to the flask:

  (I)

Pt$_2$[{(CH$_2$=CH)(CH$_3$)$_2$Si}$_2$O]$_3$

Immediately, heat generation was observed, and aging was then allowed at 80° C. for 6 hours.

The resultant reaction mixture was subjected to gas chromatography analysis (hereinafter referred to "GC analysis"), and as a result, any peak of pentamethyldisiloxane was not observed. This reaction mixture was distilled under reduced pressure to obtain 112.1 g of a fraction having a boiling point of 70° C./399 Pa (its yield to pentamethyldisiloxane=78%). This fraction was subjected to the GC analysis, and as a result, the peak of a main product having a purity of 97% (area %) was confirmed. The data regarding $^1$H-NMR spectrum, $^{13}$C-NMR, IR spectrum and GC-Mass spectrum of the thus obtained main product are as follows:

$^1$H-NMR(400 MHz,CDCl$_3$): δ ppm 0.0(Si—C$\underline{H}_3$,s,15H) 0.7(Si—C$\underline{H}_2$,dd,1H) 1.0(Si—C$\underline{H}_2$,dd,1H) 1.2(C$\underline{H}_3$,d,3H) 2.5(C$\underline{H}$,m,1H) 3.6(O—C$\underline{H}_3$,s,3H)

$^{13}$C-NMR(400 MHz,CDCl$_3$): ppm 0.7(Si—$\underline{C}$H$_3$) 1.1 (Si—$\underline{C}$H$_3$) 1.9(Si—$\underline{C}$H$_3$) 20.0($\underline{C}$H$_3$) 23.0(Si—$\underline{C}$H$_2$) 34.9($\underline{C}$H) 51.4(O—$\underline{C}$H$_3$) 178.1($\underline{C}$=O)

IRS(KBr):cm$^{-1}$ 2950(C—H) 1740(C=O) 1250(Si—C) 1050(Si—O)

GC-Mass:(m/z) 248[M$^+$]

It was confirmed from these data that the main product had the following chemical structural formula (II):

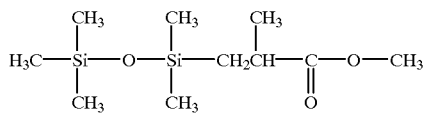

EXAMPLE 2

(Reaction of pentamethyldisiloxane and butyl methacrylate)

0.33 g (which corresponded to 1 wt % of a total feed) of 2,6-di-tert-butyl-4-methylphenol was placed in a 100 ml three-necked flask equipped with a stirring device and a condenser, and this flask was then purged with nitrogen. Furthermore, 20 ml of toluene, 7.8 g (0.055 mol) of butyl methacrylate and 7.4 g (0.05 mol) of pentamethyldisiloxane were added to the flask, and while the temperature in the flask was maintained at 80° C., 18.8 μl (2.5×10$^{-6}$ mol, 5×10$^{-5}$ mol to Si—H) of a platinum complex (3 wt % xylene solution) represented by the formula (I) was added to the flask. Immediately, heat generation was observed, and aging was then allowed at 80° C. for 3.5 hours.

The resultant reaction mixture was subjected to GC analysis, and as a result, any peak of pentamethyldisiloxane was not observed. Low-boiling components were distilled off from the reaction mixture at 80° C./266 Pa over 2 hours, thereby obtaining a residue. In this residue, a desired siloxane compound was contained at a purity of 97% (GC analysis). It was confirmed from this fact that the reaction proceeded substantially quantitatively.

The data regarding $^1$H-NMR spectrum and IR spectrum of the thus obtained siloxane compound are as follows:

$^1$H-NMR(90 MHz,CDCl$_3$): δ ppm 0.0(Si—C$\underline{H}$,s,15H) 1.0~0.6(C$\underline{H}_3$,Si—C$\underline{H}_2$,m,5H) 1.2(C$\underline{H}_3$,d,3H) 1.7~1.3(C$\underline{H}_2$,m,4H) 2.7~2.3(C$\underline{H}$,m,1H) 4.0(O—C$\underline{H}_2$,t,2H)

IR(KBr):cm$^{-1}$ 2950(C—H) 1730(C=O) 1250(Si—C) 1050(Si—O)

It was confirmed from the above data that the obtained siloxane compound had the following structural formula (III):

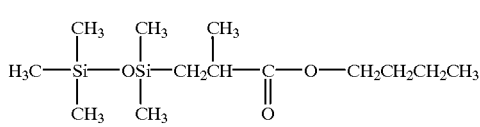

EXAMPLE 3

(Reaction of pentamethyldisiloxane and n-stearyl methacrylate)

0.42 g (which corresponded to 1 wt % of a total feed) of 2,6-di-tert-butyl-4-methylphenol was placed in a 100 ml three-necked flask equipped with a stirring device and a condenser, and this flask was then purged with nitrogen. Furthermore, 20 ml of toluene, 16.9 g (0.05 mol) of n-stearyl methacrylate and 7.4 g (0.05 mol) of pentamethyldisiloxane were added to the flask, and while the temperature in the flask was maintained at 80° C., 18.8 μl (2.5×10$^{-6}$ mol, 5×10$^{-5}$ mol to Si—H) of a platinum complex (3 wt % xylene solution) represented by the formula (I) was added to the flask. Immediately, heat generation was observed, and aging was then allowed at 80° C. for 6 hours.

The resultant reaction mixture was analyzed by infrared spectroscopic analysis (hereinafter referred to as "IR analysis"), and as a result, any absorption peak based on Si—H of pentamethyldisiloxane was not observed. Low-boiling components were distilled off from the reaction mixture at 80° C./266 Pa over 2 hours, thereby obtaining a residue. It was confirmed that a desired siloxane compound was present in an amount of 21.0 g in the residue. The data regarding $^1$H-NMR spectrum and IR spectrum of the thus obtained siloxane compound are as follows:

$^1$H-NMR(90 MHz,CDCl$_3$): δ ppm 0.0(Si—CH$_3$,s,15H) 1.0~0.6(CH$_3$,Si—CH$_2$,m,5H) 1.4~1.0(CH$_3$,CH$_2$,m,33H) 1.8~1.4(CH$_2$,m,2H) 2.7~2.3(CH,m,1H) 4.0(O—CH$_2$,t,2H)

IR(KBr):cm$^{-1}$ 2950(C—H) 1730(C=O) 1250(Si—C) 1050(Si—O)

It was confirmed from these data that the obtained siloxane compound had the following structural formula (IV):

(IV)

$$H_3C-\underset{\underset{CH_3}{|}}{\overset{\overset{CH_3}{|}}{Si}}-O-\underset{\underset{CH_3}{|}}{\overset{\overset{CH_3}{|}}{Si}}-CH_2CH-\underset{\underset{O}{\|}}{C}-O-(CH_2)_{17}-CH_3$$
$$\phantom{H_3C-Si-O-Si-CH_2}\overset{|}{CH_3}$$

EXAMPLE 4
(Reaction of pentamethyldisiloxane and glycidyl methacrylate)

0.33 g (which corresponded to 1 wt % of a total feed) of 2,6-di-tert-butyl-4-methylphenol was placed in a 100 ml three-necked flask equipped with a stirring device and a condenser, and this flask was then purged with nitrogen. Furthermore, 20 ml of toluene, 7.8 g (0.055 mol) of glycidyl methacrylate and 7.4 g (0.05 mol) of pentamethyldisiloxane were added to the flask, and while the temperature in the flask was maintained at 80° C., 18.8 μl (2.5×10$^{-6}$ mol, 5×10$^{-5}$ mol to Si—H) of a platinum complex (3 wt % xylene solution) represented by the formula (I) was added to the flask. Immediately, heat generation was observed, and aging was then allowed at 80° C. for 1.5 hours.

The resultant reaction mixture was analyzed by GC analysis, and as a result, any peak of pentamethyldisiloxane was not observed. Low-boiling components were distilled off from the thus obtained reaction mixture at 120° C./266 Pa over 2 hours, thereby obtaining a residue. In this residue, 13.8 g of a desired siloxane compound [purity=92% (GC analysis)] was contained. The data regarding $^1$H-NMR spectrum and IR spectrum of the obtained siloxane compound are as follows:

$^1$H-NMR(90 MHz,CDCl$_3$): δ ppm 0.0(Si—CH$_3$,s,15H) 1.0~0.7(Si—CH$_2$,m,2H) 1.2(CH$_3$,d,3H) 2.9~2.4(CH,CH$_2$,m,3H) 3.3~3.1(CH,m,1H) 3.9(O—CH$_2$,ddd,1H) 4.4(O—CH$_2$,ddd,1H)

IR(KBr):cm$^{-1}$ 2950(C—H) 1730(C=O) 1250(Si—C) 1050(Si—O)

It was confirmed from these data that the obtained siloxane compound had the following structural formula (V):

(V)

$$H_3C-\underset{\underset{CH_3}{|}}{\overset{\overset{CH_3}{|}}{Si}}-O-\underset{\underset{CH_3}{|}}{\overset{\overset{CH_3}{|}}{Si}}-CH_2CH-\underset{\underset{O}{\|}}{C}-O-CH_2CH\overset{\diagdown}{\underset{\diagup}{\phantom{O}}}CH_2$$
$$\phantom{H_3C-Si-O-Si-CH_2CH-C-O-CH_2CH}O$$

EXAMPLE 5
(Reaction of pentamethyldisiloxane and β-(perfluorooctyl) ethyl methacrylate)

0.24 g (which corresponded to 1 wt % of a total feed) of 2,6-di-tert-butyl-4-methylphenol was placed in a 100 ml three-necked flask equipped with a stirring device and a condenser, and this flask was then purged with nitrogen. Furthermore, 15 ml of toluene, 8.38 g (0.016 mol) of β-(perfluorooctyl)ethyl methacrylate and 2.22 g (0.015 mol) of pentamethyldisiloxane were added to the flask, and while the temperature in the flask was maintained at 80° C., 18.8 μl (2.5×10$^{-6}$ mol, 16.7×10$^{-5}$ mol to Si—H) of a platinum complex (3 wt % xylene solution) represented by the formula (I) was added to the flask. Immediately, heat generation was observed, and aging was then allowed at 80° C. for 6 hours.

The resultant reaction mixture was analyzed by the use of GC, and as a result, any peak of pentamethyldisiloxane was not observed. Low-boiling components were distilled off from the thus obtained reaction mixture at 120° C./266 Pa over 1 hour, thereby obtaining a residue. It was confirmed that a desired siloxane compound [purity=93% (GC analysis)] was contained in this residue. It was confirmed from this fact that the reaction proceeded substantially quantitatively.

The data regarding $^1$H-NMR spectrum and IR spectrum of the obtained siloxane compound are as follows:

$^1$H-NMR(90 MHz,CDC$_3$): δ ppm 0.0(Si—CH$_3$,s,9H) 0.0 (Si—CH$_3$,s,6H) 1.0~0.6(Si—CH$_2$,m,2H) 1.2(CH$_3$,d,3H) 2.3~1.6(CH,CH$_2$,m,3H) 4.3(O—CH$_2$,t,2H)

IR(KBr):cm$^{-1}$ 2950(C—H) 1740(C=O) 1250(Si—C) 1250~1150(CF$_2$,CF$_3$) 1050(Si—O)

It was confirmed from these data that the obtained siloxane compound had the following structural formula (VI):

(VI)

$$H_3C-\underset{\underset{CH_3}{|}}{\overset{\overset{CH_3}{|}}{Si}}-O-\underset{\underset{CH_3}{|}}{\overset{\overset{CH_3}{|}}{Si}}-CH_2CH-\underset{\underset{O}{\|}}{C}-O-CH_2CH_2-(CF_2)_7-CF_3$$

EXAMPLE 6
(Reaction of pentamethyldisiloxane and 2,2,3,4,4,4-hexafluorobutyl methacrylate)

0.39 g (which corresponded to 1 wt % of a total feed) of 2,6-di-tert-butyl-4-methylphenol was placed in a 100 ml three-necked flask equipped with a stirring device and a condenser, and this flask was then purged with nitrogen. Furthermore, 20 ml of toluene, 13.75 g (0.055 mol) of 2,2,3,4,4,4-hexafluorobutyl methacrylate and 7.4 g (0.05 mol) of pentamethyldisiloxane were added to the flask, and while the temperature in the flask was maintained at 80° C., 18.8 μl (2.5×10$^{-6}$ mol, 5×10$^{-5}$ mol to Si—H) of a platinum complex (3 wt % xylene solution) represented by the formula (I) was added to the flask. Immediately, heat generation was observed, and aging was then allowed at 80° C. for 4 hours.

The resultant reaction mixture was analyzed by the use of GC, and as a result, any peak of pentamethyldisiloxane was not observed. Low-boiling components were distilled off from the thus obtained reaction mixture at 70° C./266 Pa over 1 hour, thereby obtaining a residue. In this residue, 14.9 g of a desired siloxane compound was contained [purity= 70% (GC analysis)].

The data regarding $^1$H-NMR spectrum and IR spectrum of the obtained siloxane compound are as follows:

$^1$H-NMR(90 MHz,CDCl$_3$): δ ppm 0.0(Si—CH$_3$,s,9H) 0.0 (Si—CH$_3$,s,6H) 1.1~0.5(Si—CH$_2$,m,2H) 1.2(CH$_3$,d,3H) 2.9~2.5(CH,m,1H) 5.4~3.9(O—CH$_2$,CFH,m,3H)

IR(KBr):cm$^{-1}$ 2950(C—H) 1740(C=O) 1250(Si—C) 1250~1150(CF$_2$,CF$_3$) 1050(Si—O)

It was confirmed from these data obtained above that the main compound had the following structural formula (VII):

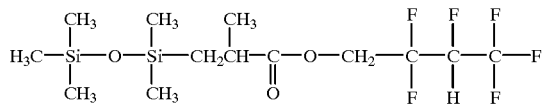

(VII)

EXAMPLE 7
(Reaction of a siloxane compound having a hydrosilyl group at an α-position and methyl methacrylate)

0.59 g (which corresponded to 1 wt % of a total feed) of 2,6-di-tert-butyl-4-methylphenol was placed in a 200 ml three-necked flask equipped with a stirring device and a condenser, and this flask was then purged with nitrogen. Furthermore, 50 ml of toluene, 5.5 g (0.065 mol) of methyl methacrylate and 52.45 g (0.05 mol) of mono functional dimethylsiloxane oligomer with Si—H group (hydrogen equivalent=1050, and hence an oligomer having a number-average molecular weight of 1050) were added to the flask. While the temperature in the flask was maintained at 80° C., 18.8 μl (2.5×10$^{-6}$ mol, 5×10$^{-5}$ mol to Si—H) of a platinum complex (3 wt % xylene solution) represented by the formula (I) was added to the flask. Immediately, heat generation was observed, and aging was then allowed at 80° C. for 18 hours.

The resultant reaction mixture was analyzed by IR analysis, and as a result, any absorption peak based on Si—H was not observed. Low-boiling components were distilled off from the thus obtained reaction mixture at 80° C./266 Pa over 1 hour, thereby obtaining a residue. In this residue, a desired siloxane compound was contained. It was confirmed that the reaction proceeded substantially quantitatively.

The data regarding $^1$H-NMR spectrum and IR spectrum of the obtained siloxane compound are as follows:

$^1$H-NMR(90 MHz,CDCl$_3$): δ ppm 0.0(Si—C$\underline{H}_3$,s,80H) 1.4~0.4(C$\underline{H}_3$,C$\underline{H}_2$,Si—C$\underline{H}_2$,m,14H) 2.7~2.4(C$\underline{H}$,m,1H) 3.6 (O—C$\underline{H}_3$,s,3H)

IR(KBr):cm$^{-1}$ 2950(C—H) 1740(C=O) 1250(Si—C) 1100~1020(Si—O)

It was confirmed from these data obtained above that the main compound had the following structural formula (VIII):

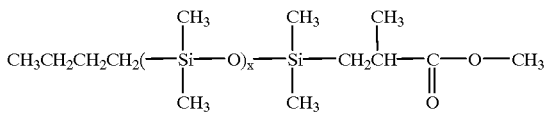

(VIII)

wherein x can be presumed to be an integer of 10 to 20.

COMPARATIVE EXAMPLE 1
(Reaction of pentamethyldisiloxane and methyl methacrylate)

0.30 g (which corresponded to 1 wt % of a total feed) of 2,6-di-tert-butyl-4-methylphenol and 23.1 mg (2.5×10$^{-5}$ mol, 5×10$^{-4}$ mol to Si—H) of a rhodium catalyst represented by the formula (IV)

RhCl(PPh$_3$)$_3$ (IV)

were placed in a 100 ml three-necked flask equipped with a stirring device and a condenser, and this flask was then purged with nitrogen. Furthermore, 20 ml of toluene and 5.5 g (0.055 mol) of methyl methacrylate were added to the flask, and while the temperature in the flask was maintained at 80° C., 7.4 g (0.05 mol) of pentamethyldisiloxane was added dropwise thereto over 1 minute. Immediately, heat generation was observed, and aging was then allowed at 80° C. for 2.5 hours.

The resultant reaction mixture was analyzed by the use of GC, and as a result, any peak of pentamethyldisiloxane was not observed. A β-silyl compound which was a desired siloxane compound was obtained merely in a low ratio of 7%, and a proportion of 85% was a 1,4 adduct represented by the following formula (X):

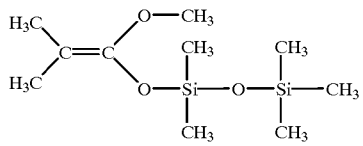

(X)

What is claimed is:

1. A siloxane compound represented by the formula (1)

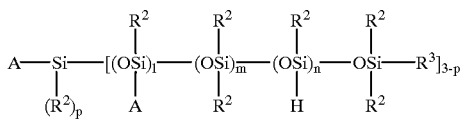

(1)

wherein R$^2$ is a methyl group or a phenyl group; R$^3$ is an alkyl group having 1 to 6 carbon atoms or A; l is an integer of 0 to 500; m is an integer of 0 to 1,000; n is an integer of 0 to 500; p is an integer of 0 to 2; and A is an ester group represented by the formula (2)

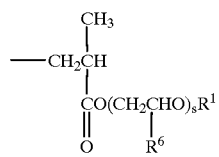

(2)

wherein R$^6$ is hydrogen or the methyl group; s is an integer of 0 to 100; and R$^1$ is a branched or a straight-chain alkyl group having 1 to 30 carbon atoms, a cyclohexyl group, a phenyl group, a benzyl group, a glycidyl group, or a fluorine-containing organic group represented by the formula (3)

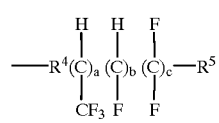

(3)

wherein R$^4$ is a saturated hydrocarbon having 0 to 6 carbon atoms, and when 0 is selected, R$^4$ is not present; R$^5$ is hydrogen or fluorine; a is 0 or 1; and b and c are each an integer of 0 to 20, but for a, b and c, 0 is not simultaneously selected.

2. A siloxane compound according to claim 1 wherein p=2 and n=0.

3. A siloxane compound according to claim 1 wherein p=2, l=0, n=0 and R²=a methyl group.

4. A siloxane compound according to claim 1 wherein p=2, l=0, n=0, R²=a methyl group, R³=a butyl group and s=0.

5. A siloxane compound according to claim 1 wherein p=2, l=0, m=0, n=0, R²=a methyl group and R³=the methyl group.

6. A siloxane compound according to claim 1 wherein p=2, l=0, m=0, n=0, s=0, R²=a methyl group and R³=the methyl group.

7. A siloxane compound according to claim 1 wherein p=2, l=0, n=0, R²=a methyl group, R³=A and s=0.

8. A method for preparing an ester group-containing siloxane compound represented by the formula (1)

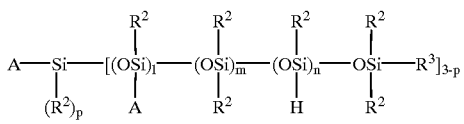
(1)

wherein R² is a methyl group or a phenyl group; R³ is an alkyl group having 1 to 6 carbon atoms or A; l is an integer of 0 to 500; m is an integer of 0 to 1,000; n is an integer of 0 to 500; p is an integer of 0 to 2; and A is an ester group represented by the formula (2)

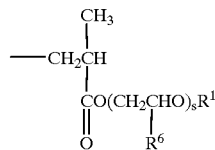
(2)

wherein R⁶ is hydrogen or the methyl group; s is an integer of 0 to 100; R¹ is a branched or a straight-chain alkyl group having 1 to 30 carbon atoms, a cyclohexyl group, a phenyl group, a benzyl group, a glycidyl group, or a fluorine-containing organic group represented by the formula (3)

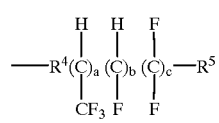
(3)

wherein R⁴ is a saturated hydrocarbon having 0 to 6 carbon atoms, and when 0 is selected, R⁴ is not present; R⁵ is hydrogen or fluorine; a is 0 or 1; and b and c are each an integer of 0 to 20, but for a, b and c, 0 is not simultaneously selected, which comprises the step of reacting, in the presence of a platinum-containing catalyst, a methacrylic acid ester compound represented by the formula (4)

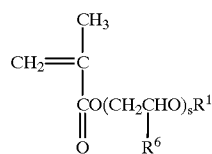
(4)

wherein R⁶ is hydrogen or the methyl group; s is an integer of 0 to 100; and R¹ is a branched or a straight-chain alkyl group having 1 to 30 carbon atoms, a cyclohexyl group, a phenyl group, a benzyl group, a glycidyl group, or a fluorine-containing organic group represented by the formula (3)

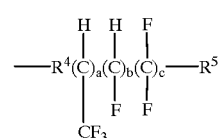
(3)

wherein R⁴ is a saturated hydrocarbon having 0 to 6 carbon atoms, and when 0 is selected, R⁴ is not present; R⁵ is hydrogen or fluorine; a is 0 or 1; and b and c are each an integer of 0 to 20, but for a, b and c, 0 is not simultaneously selected,
with a hydrosilyl group-containing siloxane compound represented by the formula (5)

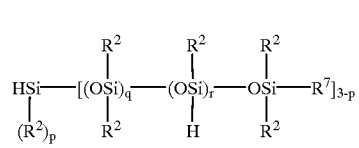
(5)

wherein R² is the methyl group or a phenyl group; R⁷ is hydrogen or an alkyl group having 1 to 6 carbon atoms; q is an integer of 0 to 1000; r is an integer of 0 to 500; and p is an integer of 0 to 2.

9. A method for preparing a siloxane compound according to claim 8 wherein p=2 and n=0.

10. A method for preparing a siloxane compound according to claim 8 wherein p=2, l=0, n=0 and R²=a methyl group.

11. A method for preparing a siloxane compound according to claim 8 wherein p=2, l=0, n=0, R²=a methyl group, R³=a butyl group and s=0.

12. A method for preparing a siloxane compound according to claim 8 wherein p=2, l=0, m=0, n=0, R²=a methyl group and R³=a methyl group.

13. A method for preparing a siloxane compound according to claim 8 wherein p=2, l=0, m=0, n=0, s=0, R²=a methyl group and R³=a methyl group.

14. A method for preparing a siloxane compound according to claim 8 wherein p=2, l=0, n=0, R²=a methyl group, R³=A and s=0.

* * * * *